US005683859A

United States Patent [19]

Nothnagle et al.

[11] Patent Number: 5,683,859
[45] Date of Patent: Nov. 4, 1997

[54] PHOTOGRAPHIC DEVELOPING COMPOSITION CONTAINING A SLUDGE INHIBITING AGENT AND USE THEREOF IN THE HIGH CONTRAST DEVELOPMENT OF NUCLEATED PHOTOGRAPHIC ELEMENTS

[75] Inventors: Ronald Joseph Nothnagle, Webster; Jeffrey Richard Sefl, Byron; Harold Ihor Machonkin, Webster, all of N.Y.

[73] Assignee: Eastman Kodak Company, Rochester, N.Y.

[21] Appl. No.: 650,675

[22] Filed: May 20, 1996

[51] Int. Cl.$^6$ ..................................... G03C 5/305
[52] U.S. Cl. .................... 430/488; 430/486; 548/130
[58] Field of Search .......................... 430/486, 488; 548/130

[56] References Cited

U.S. PATENT DOCUMENTS

| | | | |
|---|---|---|---|
| 4,371,610 | 2/1983 | Toyoda et al. | 430/488 |
| 4,798,784 | 1/1989 | Kishimoto et al. | 430/486 |
| 4,914,003 | 4/1990 | Yagihara et al. | 430/448 |
| 4,975,354 | 12/1990 | Machonkin et al. | 430/264 |
| 5,030,547 | 7/1991 | Katoh et al. | 430/264 |

FOREIGN PATENT DOCUMENTS 0940169  10/1963  United Kingdom ............ 430/488

*Primary Examiner*—Hoa Van Le
*Attorney, Agent, or Firm*—John R. Everett

[57] ABSTRACT

An improved photographic developing composition, for use in development of a black-and-white silver halide photographic element, is comprised of at least one developing agent and, in an amount sufficient to inhibit sludge deposition, mercapto thiadiazole glycerol propoxylate. The developing composition is broadly useful in black-and-white development but is most advantageously employed in a process for forming a high-contrast image utilizing a silver halide photographic element comprising a hydrazine compound which functions as a nucleating agent and an amino compound which functions as an incorporated booster.

20 Claims, No Drawings

PHOTOGRAPHIC DEVELOPING COMPOSITION CONTAINING A SLUDGE INHIBITING AGENT AND USE THEREOF IN THE HIGH CONTRAST DEVELOPMENT OF NUCLEATED PHOTOGRAPHIC ELEMENTS

FIELD OF THE INVENTION

This invention relates to photography and in particular to the development of silver halide photographic elements.

BACKGROUND OF THE INVENTION

In the development of black-and-white silver halide photographic elements a commonly encountered problem is the accumulation of "sludge" or "dirt" in the developing composition. While the mechanisms whereby such sludge is formed are varied and complex, an important contributing factor is the presence in developing compositions of compounds such as sulfites which dissolve silver halides and form silver complexes. The silver complexes that are extracted from the photographic element into the developing composition are reduced by other components of the developing composition and convened to extremely fine particles of metallic silver which are commonly referred to in the art as "silver sludge." The formation of this silver sludge is a particularly serious problem when the photographic elements are processed in an automatic processing apparatus. Thus, for example, it is common for the sludge to attach to the walls of the developing tank and/or the rollers of an automatic processor and the particles can subsequently transfer to the photographic element. The result can manifest itself as black silver specks or silver stain and, if sufficiently severe, this can render the photographic element useless for its intended purpose. The problem can be alleviated to some extent by frequent cleaning of the processing equipment to remove accumulated silver sludge, but this adds significantly to the effort and expense of the processing operation.

The problem of reducing or avoiding the deposition of silver sludge has been a very longstanding problem in the photographic art. A wide variety of compounds has been proposed heretofore as sludge-inhibiting agents. Their effectiveness for this purpose is often insufficient. Moreover, agents used to reduce sludge formation can have unwanted side effects such as suppressing development or adversely affecting the contrast of the photographic element.

Sulfites are very commonly used in black-and-white developing compositions where they serve to extend the life of the developing composition by protecting it against aerial oxidation. While they are a major contributor to sludge formation they are not the only one. Thus, for example, other common components of developing compositions such as thiosulfates and thiocyanates also dissolve silver halide and form silver complexes. Other factors contributing to sludge formation include the throughput of sensitized material, the replenishment rate and the design of the processing apparatus. Generally speaking, most, if not all, black-and-white developing compositions suffer from the problem of sludge formation, although the degree to which it occurs varies widely depending upon both the components of the developing composition and the composition of the photographic element being processed.

U.S. Pat. No. 4,975,354 issued Dec. 4, 1990, entitled "Photographic Element Comprising An Ethyleneoxy-Substituted Amino Compound And Process Adapted To Provide High Contrast Development", by Harold I. Machonkin and Donald L. Kerr, describes silver halide photographic elements having incorporated therein a hydrazine compound which functions as a nucleator and an amino compound which functions as an incorporated booster. Such elements provide a highly desirable combination of high photographic speed, very high contrast and excellent dot quality, which renders them very useful in the field of graphic arts. Moreover, since they incorporate the booster in the photographic element, rather than using a developing solution containing a booster, they have the further advantage that they are processable in conventional, low cost, rapid-access developers.

Other patents describing silver halide photographic elements comprising a hydrazine compound which functions as a nucleator and an amino compound which functions as an incorporated booster include U.S. Pat. No. 4,914,003 and U.S. Pat. No. 5,030,547.

Nucleated high-contrast photographic elements of the type described hereinabove are particularly prone to the formation of silver sludge. While the reason for this is not clearly understood, it has been a significant factor hindering the commercial utilization of such otherwise advantageous photographic elements in the field of graphic arts.

The present invention is directed toward the objective of providing an improved developing composition, useful with a wide variety of black-and-white silver halide photographic elements, that has less tendency to deposit sludge than developing compositions utilized heretofore. It is a particular objective of the invention to provide an improved process for developing high contrast photographic elements, containing a hydrazine compound which functions as a nucleator and an amino compound which functions as an incorporated booster, utilizing the improved black-and-white developing composition of this invention.

SUMMARY OF THE INVENTION

This invention provides a photographic developing composition, for use in development of a black-and-white silver halide photographic element, which comprises at least one developing agent and, in an amount sufficient to inhibit sludge deposition, a mercapto thiadiazole glycerol propoxylate of according to structure 1:

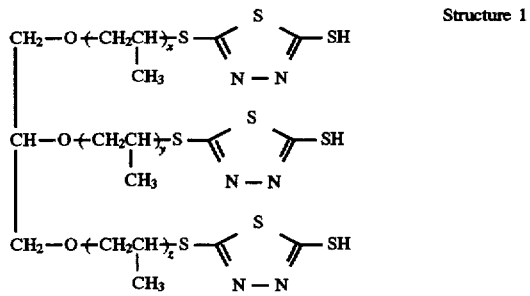

Structure 1 and x+y+z is 2.8 to 3.2.

It is preferred that the mercapto thiadiazole glycerol propoxylate of structure 1 have a molecular weight of at least 484 and preferably in the range of 400 to 5000.

The following protocol was used to prepare a mercapto thiadiazole glycerol propoxylate of Structure 1 wherein x+y+z is approximatelyimately 3.

1. Equip a 100 mL 3 neck flask with an air driven overhead stirrer, thermometer, condenser, addition funnel, and ice/salt water bath.
2. Charge 10.0g (0.040 mol.) DOW Polyol PT 250, 14.01 g(19.2 mL, 0.138 mol.) triethylamine, and 25 mL propyl acetateto the flask. Cool the resulting clear solution to approximately 0° C.

3. Add 15.40 g (10.2 mL., 0.134 mol.) methanesulfonyl chloride in a dropwise manner over 45 minutes 15 10°–0° C. The addition is exothermic and off white solids (triethylamine hydrochloride) form (and become thick) as the addition proceeds. When the addition is complete, remove the cooling bath and let the slurry warm to ambient temperature, stir 30 minutes.

4. Filter directly into a 250 mL 3 neck flask, rinse the 100 mL flask and the triethylamine hydrochloride collected on the filter funnel with 25 mL of propyl acetate. The volume of the filtrate is approximately 45 mL. here.

5. Equip the 250 mL 3 neck flask containing the filtrate (from above) with an air driven overhead stirrer, thermometer, reflux condenser, and constant temperature bath. Add 80 mL (62.9 g) isopropyl alcohol (IPA), and 24.0 g (0.16 mol.) dimercaptothiadiazole(DMTD) to the trimesylate solution in the flask.

6. Add 6.00 g (0.081 mol.) calcium hydroxide to the yellow slurry. This reaction is exothermic of approximatelyimately 20° C. (temp to 38° C.) as the basic calcium hydroxide reacts with the acidic DMTD. Let this exotherm occur without external cooling.

7. Heat the reaction in a 75° C. constant temperture bath (reaction temp 72° C.) for 16 hours (overnight). A thin yellow slurry results.

8. Distill the propyl acetate (PrOAc) and IPA solvent mixture from 81°–83° C. under atmospheric pressure. Apply aspirator vacuum slowly at the end until a thick yellow goo (approximately 50 mL volume) remains in the flask (85 mL of solvent collected).

9. Add 70 mL PrOAc to the yellow residue, warm to 50° C., and stir to a uniform slurry. Filter the fine yellow solids, and rinse with 20 mL PrOAc.

10. Wash residual calcium salts out of the PrOAc solution with the following water washes. Wash #1: Add 10 mL. of water to the above filtrate, stir and separate layers. Recover 9 mL. of aqueous layer. Wash #2: Add 10 mL. water and separate as above. Recover 12 mL. of the lower layer. Wash #3: Add 10 mL. water and separate as above. Recover 11.5 of the lower layer.

11. Azeotropically distill under atmospheric pressure (81°–92° C.) until approximatelyimately 35 mL. has been collected (about 2 mL. of water separates in the distillate), or until the temperature has risen from approximately 81° C. to 92° C. Add 25 mL PrOAc and continue distilling until the distillation temperature reaches approximately 94° C. and distillation slows almost to a stop, (full steam bath heating).

12. Slowly apply aspirator vacuum and remove most of the remaining PrOAc until the volume in the flask is approximately 50 mL.

13. Add 100.0 g (89.4 mL) di(ethylene glycol). Rinse all of the weighed di(ethylene glycol) into the flask with approximatelyimately 20 mL propyl acetate. Warm to approximately 50° C. and filter through glass fiber to remove any traces of remaining solids.

14. Slowly apply aspirator vacuum to the solution and collect the distilling propyl acetate. Warm the orange solution to 80° C. When no more distillate condenses, hold at 75°–80° C. with good stirring for 30 minutes under full aspirator vacuum. This is to remove all of the remaining PrOAc and IPA solvents.

15. Cool the hazy, orange-red solution to approximately 40° C., and release vacuum. Recover a 124.9 g of a di(ethylene glycol) solution of mercapto thiadiazole glycerol propoxylate of Structure 1 wherein x+y+z is approximately3.

The invention also includes within its scope a process for forming a high-contrast photographic image comprising the steps of (1) imagewise exposing a silver halide photographic element and (2) developing the exposed element with a developing composition, wherein the photographic element contains a hydrazine compound which functions as a nucleating agent and an amino compound which functions as an incorporated booster and wherein the developing composition comprises at least one developing agent and, in an amount sufficient to inhibit sludge deposition, a mercapto thiadiazole glycerol propoxylate.

The developing compositions of this invention are useful for forming black-and-white silver images by development of light-sensitive silver halide photographic elements of many different types, including, for example, microfilms, aerial films and X-ray films. They are especially useful in the field of graphic arts for forming very high contrast silver images. In the graphic arts field, they can be used with a wide variety of graphic arts films in addition to those specifically described in U.S. Pat. No. 4,975,354.

DETAILED OF THE INVENTION

The mercapto thiadiazole glycerol propoxylates of structure 1 are used in any amount sufficient to inhibit sludge deposition. Such mercapto thiadiazole glycerol propoxylate according to are known.

In the developer compositions of this invention, the mercapto thiadiazole glycerol propoxylate is typically employed in an amount sufficient to provide a concentration of from about 0.05 to about 10 grams per liter of working strength developing solution, more preferably from about 0.1 to about 6 grams per liter and most preferably from about 0.1 to about 2 grams per liter. The optimum amount to be used will depend upon both the other components of the developing composition and the particular photographic element which is to be processed as well as on the particular mercapto thiadiazole glycerol propoxylate utilized.

The present invention is most effectively employed in conjunction with or without the use of an in-line filter through which the developing solution is recirculated. While applicants do not wish to be bound by any theoretical explanation of the manner in which their invention functions, it is believed that the mercapto thiadiazole glycerol propoxylate functions in the developing solution to bind cationic silver ions to form a soluble in solution complex that will not for form silver insoluble complexes. The effect of utilizing a mercapto thiadiazole glycerol propoxylate is to render the photographic developer solution cleaner working. In practice the can be introduced to the developing solution at manufacturing as a concentrate, prior to use as a concentrate, prior to use as in a working strength developing solution or added intermittently during the operation of the photographic processor.

In the practice of this invention, the mercapto thiadiazole glycerol propoxylate is preferably added to the developer concentrate during manufacture.

In the field of graphic arts, it has long been known to achieve high contrast by the use of low sulfite "lith" developers. In conventional "lith" developers, high contrast is achieved using the "lith effect" (also referred to as infectious development) as described by J. A. C. Yule in the Journal of the Franklin Institute, Vol. 239, 221–230 (1945). This type of development is believed to proceed autocatalytically. To achieve "lith effect" development, a low, but critical concentration of free sulfite ion is maintained by use of an aldehyde bisulfite adduct, such as sodium formaldehyde bisulfite, which, in effect, acts as a sulfite ion buffer. The low sulfite ion concentration is necessary to avoid interference with the accumulation of developing agent oxidation products, since such interference can result in prevention of infectious development. The developer typically contains only a single type of developing agent, namely, a developing agent of the dihydroxybenzene type, such as hydroquinone.

Photographic elements utilizing a hydrazine compound that functions as a nucleating agent are not ordinarily processed in conventional "lith" developers but in developers that contain substantially higher amounts of sulfite as described, for example, in such Patents as U.S. Pat. Nos. 4,269,929, 4,914,003, 4,975,354 and 5,030,547. Developers which contain high concentrations of sulfite are especially prone to the deposition of silver sludge.

The novel photographic developing composition of this invention includes at least one of the conventional developing agents utilized in black-and-white processing. Such developing agents include dihydroxybenzene developing agents, ascorbic acid developing agents, aminophenol developing agents, and 3-pyrazolidone developing agents.

The dihydroxybenzene developing agents which can be employed in the developing compositions of this invention are well known and widely used in photographic processing. The preferred developing agent of this class is hydroquinone. Other useful dihydroxybenzene developing agents include:

chlorohydroquinone,
bromohydroquinone,
isopropylhydroquinone,
toluhydroquinone,
methylhydroquinone,
2,3-dichlorohydroquinone,
2,5-dimethylhydroquinone,
2,3-dibromohydroquinone,
1,4-dihydroxy-2-acetophenone-2,4-dimethyl-hydroquinone
2,5-diethylhydroquinone,
2,5-di-p-phenethylhydroquinone,
2,5-dibenzoylarninohydroquinone,
2,5-diacetaminohydroquinone, and the like.

Ascorbic acid developing agents have been utilized heretofore in a wide variety of photographic developing processes. Thus, for example, U.S. Pat. Nos. 2,688,548 and 2,688,549 disclose developing compositions containing ascorbic acid developing agents and 3-pyrazolidone developing agents; U.S. Pat. No. 3,022,168 discloses developing compositions containing ascorbic acid developing agents and activating developers such as N-methyl-p-aminophenol; U.S. Pat. No. 3,512,981 discloses developing compositions containing a dihydroxybenzene developing agent such as hydroquinone, a sulfite and an ascorbic acid developing agent; U.S. Pat. No. 3,870,479 discloses a lithographic-type diffusion transfer developer containing an ascorbic acid developing agent; U.S. Pat. No. 3,942,985 describes developing solutions containing an ascorbic acid developing agent and an iron chelate developer; U.S. Pat. Nos. 4,168, 977, 4,478,928 and 4,650,746 disclose the use of an ascorbic acid developing agent in processes in which a high contrast photographic element is developed in the presence of a hydrazine compound; U.S. Pat. Nos. 4,839,259 and 4,997, 743 disclose high contrast photographic elements containing a hydrazine compound and an incorporated ascorbic acid developing agent, and U.S. Pat. No. 4,975,354 discloses the use of an ascorbic acid developing agent in developing high contrast photographic elements containing both a hydrazine compound that functions as a nucleating agent and an amino compound that functions as an incorporated booster.

By the term "an ascorbic acid developing agent", as used herein, it is intended to include ascorbic acid and the analogues, isomers and derivatives thereof which function as photographic developing agents. Ascorbic acid developing agents are very well known in the photographic art (see the references cited hereinabove) and include, for example, the following compounds:

L-ascorbic acid
D-ascorbic acid
L-erythroascorbic acid
D-glucoascorbic acid
6-desoxy-L-ascorbic acid
L-rhamnoascorbic acid
D-glucoheptoascorbic acid
imino-L-erythroascorbic acid
imino-D-glucoascorbic acid
imino-6-desoxy-L-ascorbic acid
imino-D-glucoheptoascorbic acid
sodium isoascorbate
L-glycoascorbic acid
D-galactoascorbic acid
L-araboascorbic acid
sorboascorbic acid
sodium ascorbate
and the like.

Developing compositions which utilize a primary developing agent, such as a dihydroxybenzene developing agent or an ascorbic acid developing agent, frequently also contain an auxiliary super-additive developing agent. Examples of useful auxiliary super-additive developing agents are aminophenols and 3-pyrazolidones.

The auxiliary super-additive developing agents which can be employed in the developing compositions of this invention are well known and widely used in photographic processing. As explained in Mason, "Photographic Processing Chemistry", Focal Press, London, 1975, "super-additivity" refers to a synergistic effect whereby the combined activity of a mixture of two developing agents is greater than the sum of the two activities when each agent is used alone in the same developing solution (Note especially the paragraph entitled, "Superadditivity" on Page 29 of Mason).

For the purposes of this invention, the preferred auxiliary super-additive developing agents are the 3-pyrazolidone developing agents. Particularly preferred developing agents of this class are disclosed in U.S. Pat. No. 5,457,011. The most commonly used developing agents of this class are 1-phenyl-3-pyrazolidone, 1-phenyl-4,4-dimethyl-3-pyrazolidone, 1-phenyl-4-methyl-4-hydroxymethyl-3-pyrazolidone and 1-phenyl-4,4-dihydroxymethyl-3-pyrazolidone. Other useful 3-pyrazolidone developing agents include:

1-phenyl-5-methyl-3-pyrazolidone,
1-phenyl-4,4-diethyl-3-pyrazolidone,
1-p-aminophenyl-4-methyl-4-propyl-3-pyrazolidone,
1-p-chlorophenyl-4-methyl-4-ethyl-3-pyrazolidone,
1-p-acetamidophenyl-4,4-diethyl-3-pyrazolidone,
1-p-betahydroxyethylphenyl-4,4-dimethyl-3-pyrazolidone, 1-p-hydroxyphenyl-4,4-dimethyl-3-pyrazolidone, 1-p-methoxyphenyl-4,4-diethyl-3-pyrazolidone, 1-p-tolyl-4,4-dimethyl-3-pyrazolidone, and the like.

Useful auxiliary super-additive developing agents for use in the aqueous alkaline developing compositions of this invention are aminophenols. Examples of useful aminophenols include:

p-aminophenol o-aminophenol

N-methylaminophenol 2,4-diaminophenol hydrochloride

N-(4-hydroxyphenyl)glycine p-benzylaminophenol hydrochloride 2,4-diamino-6-methylphenol 2,4-diaminoresorcinol N-(beta-hydroxyethyl)-p-aminophenol, and the like.

More than one primary developing agent can be used in the developing compositions of this invention. For example, the developing composition can contain two different dihydroxybenzene developing agents or two different ascorbic acid developing agents or both a dihydroxybenzene developing agent and an ascorbic acid developing agent. More than one auxiliary super-additive developing agent can be included in the developing compositions of this invention. For example, the developing compositions can contain two different aminophenol developing agents or two different 3-pyrazolidone developing agents or both an aminophenol developing agent and a 3-pyrazolidone developing agent.

In addition to one or more developing agents and the mercapto thiadiazole glycerol propoxylate, the novel developing compositions of this invention preferably also contain a sulfite preservative.

By the term "sulfite preservative" as used herein is meant any sulfur compound that is capable of forming sulfite ions in aqueous alkaline solution. Examples of such compounds include alkali metal sulfites, alkali metal bisulfites, alkali metal metabisulfites, sulfurous acid and carbonyl-bisulfite adducts.

Examples of preferred sulfites for use in the developing solutions of this invention include sodium sulfite ($Na_2SO_3$), potassium sulfite ($K_2SO_3$), lithium sulfite ($Li_2SO_3$), sodium bisulfite ($NaHSO_3$), potassium bisulfite ($KHSO_3$), lithium bisulfite ($LiHSO_3$), sodium metabisulfite ($Na_2S_2O_5$), potassium metabisulfite ($K_2S_2O_5$), and lithium metabisulfite ($Li_2S_2O_5$).

The carbonyl-bisulfite adducts which are useful in this invention are well-known compounds. See U.S. Pat. No. 5,457,011.

The amount of primary developing agent incorporated in the working strength developing solution can vary widely as desired. Typically, amounts of from about 0.05 to about 1.0 moles per liter are useful. Preferably, amounts in the range of from 0.1 to 0.5 moles per liter are employed.

The amount of auxiliary super-additive developing agent utilized in the working strength developing solution can vary widely as desired. Typically, amounts of from about 0.001 to about 0.1 moles per liter are useful. Preferably, amounts in the range of from 0.002 to 0.01 moles per liter are employed.

The amount of sulfite preservative utilized in the working strength developing solution can vary widely as desired. Typically, amounts of from about 0.05 to about 1.0 moles per liter are useful. Preferably amounts in the range of from 0.1 to 0.5 moles per liter are employed.

Working strength developing solutions prepared from the developing compositions of this invention typically have a pH in the range of from 8 to 13 and preferably in the range of from 9 to 11.5.

As indicated hereinabove, the deposition of silver sludge is a particularly serious problem with photographic elements that are processed in automatic machine processing equipment. Such devices employ numerous conveyance rollers on which silver sludge can deposit and from which it can transfer to the photographic element being processed. Automatic processing equipment utilizing conveyance rollers is very well known in the art and is described, for example, in U.S. Pat. Nos. 3,025,779, 3,545,971 and 4,310,622.

While the essential ingredients of the novel developing composition of this invention are at least one developing agent and at least one mercapto thiadiazole glycerol propoxylate according to structure 1, a variety of other optional ingredients can also be advantageously included in the developing composition. For example, the developing composition can contain one or more antifoggants, antioxidants, sequestering agents, stabilizing agents or contrast-promoting agents. Such materials and preferred way of using them are described in U.S. Pat. No. 5,457,011.

Examples of particularly useful contrast-promoting agents are amino compounds as described, for example, in U.S. Pat. No. 4,269,929.

Examples of useful stabilizing agents are a-ketocarboxylic acids as described, for example, in U.S. Pat. No. 4,756,997.

In processing photographic elements with the developing compositions described herein, the time and temperature employed for development can be varied widely. Typically, the development temperature will be in the range of from about 20° C. (68° F.) to about 50° C. (122° F.), more preferably in the range of from about 25° C. (77° F.) to about 40° C. (104° F.), while the development time will be in the range of from about 10 seconds to about 150 seconds, more preferably in the range of from about 20 seconds to about 120 seconds.

To prevent bacterial growth, a biocide can be included in the developer concentrate. Biocides that are especially useful for this purpose are the thiazole compounds, particularly isothiazolines such as 1,2-benzisothiazolin-3-one, $_2$-methyl-4-isothiazolin-3-one, 2-octyl-4-isothiazolin-3-one and 5-chloro-N-methyl-4-isothiazolin-3-one.

Photographic systems depending on the conjoint action of a hydrazinc compound that functions as a nucleating agent and an amino compound that functions as an incorporated booster are exceedingly complex and their successful utilization is critically dependent on being able to adequately control numerous properties including speed, contrast, dot quality, pepper fog, image spread, discrimination and practical density point. Such systems are strongly influenced not only by the composition of the photographic element but by the composition of the developing solution and by such factors as development pH, development time and development temperature.

The goal of achieving low pepper fog is one which is exceptionally difficult to achieve without sacrificing other desired properties such as speed and contrast. (The term "pepper fog" is commonly utilized in the photographic art, and refers to fog of a type characterized by numerous fine black specks). A particularly important film property is "discrimination", a term which is used to describe the ratio of the extent of shoulder development to pepper fog level. Good discrimination, i.e., full shoulder development with low pepper fog, is necessary to obtain good halftone dot quality.

Any significant level of pepper fog is highly undesirable. Image spread is an additional undesirable consequence of the autocatalytic nucleation process. Development within an area of exposure, such as a halftone dot or a line, triggers nucleation at the dot or line edge to cause the dot or line to increase in size. The nucleated development outside the original exposed area, in turn, triggers further nucleation and the growth process continues with time of development at essentially a constant rate.

Any hydrazine compound that functions as a nucleator, is capable of being incorporated in the photographic element, and is capable of acting conjointly with the incorporated booster to provide high contrast, can be used in the practice of this invention. Many of such compounds are disclosed in U.S. Pat. No. 5,457,011. Typically, the hydrazine compound is incorporated in a silver halide emulsion used in forming the photographic element. Alternatively, the hydrazine compound can be present in a hydrophilic colloid layer of the photographic element, preferably a hydrophilic colloid layer which is coated to be contiguously adjacent to the emulsion layer in which the effects of the hydrazine compound are desired. It can, of course, be present in the photographic element distributed between or among emulsion and hydrophilic colloid layers, such as undercoating layers, interlayers and overcoating layers.

One photographic system in which this invention is useful employs a hydrazine compound as a nucleating agent and an amino compound as an incorporated booster. Amino compounds which are particularly effective as incorporated boosters are described in Machonkin and Kerr, U.S. Pat. No. 4,975,354, issued Dec. 4, 1990. Other photographic systems will also find the developers provided by the invention useful. The silver halide in the photosensitive layers can be silver chloride, silver bromide, or silver iodobromide, etc.

Mercapto thiadiazole glycerol propoxylates have little or no adverse effect on the speed or other sensitometric properties of the photographic element. This is the case with both nucleated elements of the type described hereinabove and with conventional non-nucleated elements.

The invention is further illustrated by the following examples of its practice.

EXAMPLES 1–3

To evaluate the performance of mercapto thiadiazole glycerol propoxylate according to Structure 1 in inhibiting sludge deposition, tests were conducted in which the photographic element is essentially the same as that described in Example 1 of U.S. Pat. No. 5,238,779 was processed in automatic processing equipment using in control tests (Controls 1–3), a developing composition which did not contain a mercapto thiadiazole glycerol propoxylate and in tests of the invention (Examples 1–3), the same developing composition to which a mercapto thiadiazole glycerol propoxylate of Structure 1 (x+y+z is approximately 3) was added in an amount of 0.15 grams per liter of working strength developer solution.

As described in Example 1 of U.S. Pat. No. 5,238,779, the photographic element contained both a hydrazine compound which functions as a nucleating agent and an amino compound which functions as an incorporated booster.

In carrying out these tests, the following developer concentrate was prepared in accordance with the following formulation:

| Developer Concentrate | |
|---|---|
| Sodium metabisulfite | 145 g |
| 45% Potassium hydroxide | 178 g |
| Diethylenetriamine pentaacetic acid pentasodiium salt (40%) solution) | 15 g |
| Sodium bromide | 12 g |
| Hydroquinone | 65 g |
| 1-Phenyl-4-hyldroxymethlyl-4-methyl-3-pyrazolidone | 2.9 g |
| Benzotriazole | 0.4 g |
| 1-Phenyl-5-mercaptotetrazole | 0.05 g |
| 50% Sodium hydroxide | 46 g |
| Boric acid | 6.9 g |
| Diethylene glycol | 120 g |
| 67% Potassium Carbonate | 120 g |
| Water to one liter | |

The concentrate was diluted at a ratio of one part of concentrate to two parts of water to produce a working strength developing solution with a pH of 10.4±0.1.

In each of Examples 1–3, the working strength developer solution additionally contained 0.15 grams per liter of the mercapto thiadiazole glycerol propoxylate.

In both the control tests and the examples, the condition of the developing solution and processor was rated in accordance with the following cleanliness rating scale:

| Cleanliness Rating | Condition |
|---|---|
| 1 | Essentially no dirt buildup. |
| 2 | Some dirt buildup but processor is usable. |
| 3 | Dirt buildup is heavy but processor is usable. |
| 4 | Dirt buildup is very heavy and use of processor is marginal |
| 5 | Dirt buildup is extremely heavy and processor is not usable due to sludge deposits. |

The results obtained in Examples 1–3 and their associated controls are reported below. The difference between the examples was the use of different processing equipment, different film throughput rates and different run lengths, since the same film and the same developing solution was used in each example.

| Example | Cleanliness Rating |
|---|---|
| Control 1 | 3–4 |
| Example 1 | 1 |
| Control 2 | 2–3 |
| Example 2 | 1 |
| Control 3 | 2 |
| Example 3 | 1 |

As indicated by the above data, the mercapto thiadiazole glycerol propoxylate was very effective in inhibiting sludge deposition under a variety of processing conditions. Similar results were obtained when the tests were repeated using higher or lower concentrations of the mercapto thiadiazole glycerol propoxylate.

The invention has been described in detail, with particular reference to certain preferred embodiments thereof, but it should be understood that variations and modifications can be effected within the spirit and scope of the invention.

We claim:

1. A mercapto thiadiazole glycerol propoxylate of the formula:

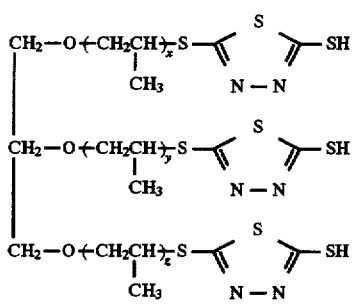

and x+y+z is 2.8 to 3.2.

2. A photographic developing composition for use in development of a black-and-white silver halide photographic element; said composition comprising at least one developing agent and, in an amount sufficient to inhibit sludge deposition, a mercapto thiadiazole glycerol propoxylate of the formula:

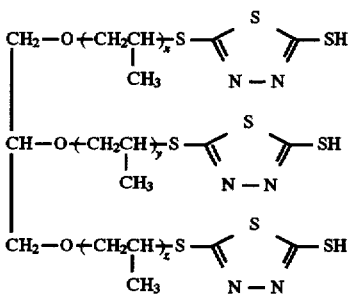

and x+y+z is 2.8 to 3.2.

3. A photographic developing composition as claimed in claim 2, wherein said mercapto thiadiazole glycerol propoxylate has molecular weight of at 484.

4. A photographic developing composition as claimed in claim 2, wherein said mercapto thiadiazole glycerol propoxylate has a molecular weight of 400 to 5000.

5. A photographic developing composition as claimed in claim 2, wherein said composition comprises a dihydroxybenzene developing agent.

6. A photographic developing composition as claimed in claim 2, wherein said composition comprises an ascorbic acid developing agent.

7. A photographic developing composition as claimed in claim 2, wherein said composition comprises a dihydroxybenzene developing agent and a 3-pyrazolidone which functions as an auxiliary super-additive developing agent.

8. A photographic developing composition as claimed in claim 2, wherein said composition comprises a dihydroxybenzene developing agent and an aminophenol which functions as an auxiliary super-additive developing agent.

9. A photographic developing composition as claimed in claim 2, wherein said composition comprises an ascorbic acid developing agent and a 3-pyrazlidone which functions as an auxilary super-additive developing agent.

10. A photographic developing composition as claimed in claim 2, wherein said composition comprises an ascorbic acid developing agent and an aminophenol which functions as an auxiliary super-additive developing agent.

11. A photographic developing composition as claimed in claim 2, wherein said composition comprises hydroquinone.

12. A photographic developing composition as claimed in claim 2, wherein said composition comprises L-ascorbic acid.

13. A photographic developing composition as claimed in claim 2, wherein said composition comprises D-ascorbic acid.

14. A photographic developing composition as claimed in claim 2, wherein said composition comprises hydroquinone and 1-phenyl-4-hydroxymethyl-4-methyl-3-pyrazolidone.

15. A photographic developing composition as claimed in claim 2, wherein said composition comprises hydroquinone and N-methylaminophenol.

16. A photographic developing composition as claimed in claim 2, additionally comprising a sulfite preservative.

17. A photographic developing composition as claimed in claim 2, where said mercapto thiadiazole glycerol propoxylate is present in an amount sufficient to provide a concentration of from about 0.5 to about 1 grams per liter of working strength developing solution.

18. A photographic developing composition for use in development of a black-and-white silver halide photographic element, said developing composition comprising:

(1) a dihydroxybenzene developing agent;

(2) an auxiliary super-additive developing agent;

(3) a sulfite preservative; and (4) a sludge-inhibiting amount of mercapto thiadiazole glycerol propoxylate according to claim 2.

19. A method of inhibiting the deposition of sludge in a photographic developing composition which comprises at least one developing agent and is adapted for use in development of a black-and-white silver halide photographic element; said method comprising incorporating in said developing composition, in an amount sufficient to inhibit sludge deposition, mercapto thiadiazole glycerol propoxylate according to claim 2.

20. A process for forming a high contrast photographic image comprising the steps of:

(1) imagewise exposing a silver halide photographic element, and (2) developing said exposed element with a developing composition;

wherein said photographic element contains a hydrazine compound which functions as a nucleating agent and an amino compound which functions as an incorporated booster;

and wherein said developing composition comprises at least one developing agent and, in an amount sufficient to inhibit sludge deposition, mercapto thiadiazole glycerol propoxylate according to claim 2.

* * * * *